(12) United States Patent
Platzek et al.

(10) Patent No.: US 6,545,135 B2
(45) Date of Patent: Apr. 8, 2003

(54) PROCESS FOR THE PRODUCTION OF PERBENZYLATED 1-O-GLYCOSIDES

(75) Inventors: Johannes Platzek, Berlin (DE); Ulrich Niedballa, Berlin (DE); Peter Mareski, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/801,050

(22) Filed: Mar. 8, 2001

(65) Prior Publication Data

US 2002/0002274 A1 Jan. 3, 2002

Related U.S. Application Data

(60) Provisional application No. 60/234,948, filed on Sep. 26, 2000.

(30) Foreign Application Priority Data

Mar. 10, 2000 (DE) .......................................... 10013328

(51) Int. Cl.$^7$ .......................... C07H 15/00; C07H 17/00
(52) U.S. Cl. ...................... 536/17.4; 536/4.1; 536/18.6; 536/124; 536/120; 536/116; 536/123; 536/123.1
(58) Field of Search ................................ 536/4.1, 18.6, 536/17.4, 124, 120, 116, 123, 123.1

(56) References Cited

U.S. PATENT DOCUMENTS 5,874,411 A   2/1999   Srivastava et al.

FOREIGN PATENT DOCUMENTS

EP   0 882 733 A   12/1998
WO   WO 01/68659   *   9/2001

OTHER PUBLICATIONS

Schmidt et al., "1–O–alkylation of D–glucopyranose." J. carbohydr. Chem. 39(1), pp. 67–84, 1984.*
Dreux et al., "Synthesis of glycosides. Direct high–performance liquid chromatographic determination of intermediate perbenzylated anomers." J. Chromatogr., 204, pp. 207–211, 1981.*
Sugawara T. et al, "Synthesis of (methoxycarbonyl)alkyl and 9–(methoxycarbonyl)–3, 6–dixanonyl glycopyranosides for the preparation of carbohydrate glycopyranosides for the preparation of carbohydrate–protein conjugates", Carbohydr. Res., Bd. 20, Nr. 1, 1992, Seiten 117–150.

Schmidt R. R., "Neue Methoden zur Glycosid–und Oligosaccaridsynthese– gibt es Alternativen zur Koenigs–Khorr–Methode?", Angew. Chemie, Bd. 98, 1986, Seiten 213–236.
Schmidt, Richard R. et al, "O–Alkylation at the anomeric center. Part 5. 1–0– Alkylation of D–glucopyranose", J. Carbohydr. Chem., (1984), 3(1), p.67–84.
Lockhoff O., "An access to glycoconjugate libraries through multicomponent reactions", Angew. Chem. Int. Ed., Bd. 37, Nr. 24, 1998, Seiten 3436–3439.

* cited by examiner

Primary Examiner—Samuel Barts
Assistant Examiner—Devesh Khare
(74) Attorney, Agent, or Firm—Millen, White, Zelano & Branigan, P.C.

(57) ABSTRACT

The invention relates to a process for the production of perbenzylated 1-O-glycosides of general formula I or salts thereof

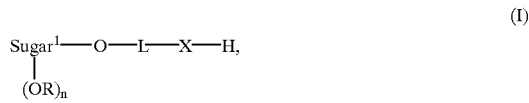

(I)

in which sugar$^1$ is a monosaccharide that is functionalized in 1-OH-position,

R represents benzyl, n means 2, 3 or 4, means —O—, —S—, —COO— or —NH— and

L means a straight-chain, branched, saturated or unsaturated $C_1$–$C_{30}$ carbon chain, which optionally is interrupted or substituted by groups.

The process according to the invention starts from economical starting materials, provides good yields and allows the production of perbenzylated saccharides with 1-O-functionalized side chains on an enlarged scale.

11 Claims, No Drawings

PROCESS FOR THE PRODUCTION OF PERBENZYLATED 1-O-GLYCOSIDES

This application claims the benefit of the filing date of U.S. Provisional Application Ser. No. 60/234,948 filed Sep. 26, 2000, which is incorporated by reference herein in its entirety.

DESCRIPTION

The invention relates to a new process for the production of perbenzylated 1-O-glycosides of general formula I, which is characterized in more detail in the claims. The process according to the invention starts from economical starting materials, provides good yields and allows the production of perbenzylated saccharides with 1-O-functionalized side chains on an enlarged scale.

Perbenzylated saccharide derivatives are valuable intermediate products in synthetic chemistry. Primarily pharmaceutical chemistry uses such components very frequently, since many highly potent and selective pharmaceutical agents carry sugar radicals. Thus, for example, in the Journal of Drug Targeting 1995, Vol. 3, pp. 111–127, applications of the so-called "glycotargeting" are described. So-called "multi-antennary sugar chains" are described in Chemistry Letters 1998, p. 823. By clustering sugar units, the carbohydrate-receptor-interaction in the case of the cell-cell-interaction is considerably improved. The synthesis of galactosides with high affinity to the asialoglycoprotein receptor is published in J. Med. Chem. 1995, 38, p. 1538 (see also Int. J. Peptide Protein Res. 43, 1994, p. 477). Here, derivatized galactoses with functionalized side chains are produced, which then can be suspended on various other molecules. A good survey on the use of saccharides as a basis of glycobiology has been provided in Acc. Chem. Res. 1995, 321. Also, for the synthesis of LewisX mimetic agents (Tet. Lett. Vol. 31, 5503), functionalized monosaccharides are used as precursors (see also JACS 1996, 118, 6826).

The use of derivatized monosaccharides as intermediate stages for potential pharmaceutical agents has been well represented in Current Medicinal Chemistry, 1995, 1, 392. Perbenzylated-1-OH-sugar derivatives (galactose, glucose) are also used in the synthesis of heart-active glycosides (digitoxin-conjugates). The 1-O-glycosylation is carried out here via trichloroacetimidate and $BF_3$-catalysis (J. Med. Chem. 1986, 29, p. 1945). For the production of immobilized sugar ligands (e.g., linkage to HSA), functionalized, protected monosaccharides are used (Chemical Society Reviews 1995, p. 413).

It is the purpose of a group of syntheses to introduce additional functionality into a sugar molecule via a 1-O-glycosylation reaction. Here, primarily terminal COOH—, amino- or OH— groups are of interest, since the latter can be further reacted in subsequent steps.

The production of 1-O-glycosides is carried out in most cases according to standard methods, such as, e.g., according to the trichloroacetimidate methods described by Koenigs-Knorr, Helferich or by R. R. Schmidt [W. Koenigs and E. Knorr, Ber. dtsch. Chem. Ges. 34 (1901) 957; B. Helferich and J. Goendeler, Ber. dtsch., Chem. Ges. 73, (1940) 532; B. Helferich, W. Piel and F. Eckstein, Chem. Ber. 94 (1961), 491; B. Helferich and W. M. Müller, Chem. Ber. 1970, 103, 3350; G. Wulff, G. Röhle and W. Krüger, Ang. Chem. Internat. Edn., 1970, 9, 455; J. M. Berry and G. G. S. Duthon, Canad. J. Chem. 1972, 50, 1424; R. R. Schmidt, Angew. Chem. 1986, 98, 213.]

A feature that is common to all of these methods is that the 1-hydroxyl group is converted into a reactive form that is ultimately used as a leaving group. Under Lewis acid catalysis (partially in stoichiometric amount), the actual reaction is carried out with an alcohol to 1-O-glycoside. For such reactions, numerous examples are provided in the literature.

In the production of immunostimulant KRN-7000 (Kirin Brewery), the condensation of tetra-O-benzyl-β-D-galactopyranosyl-bromide with a primary alcohol, whose hydroxyl group sits at the end of a di-hydroxy-amido-C-chain (in DMF/toluene under Lewis acid catalysis), is thus a central step (Drug of the Future 1997, 22(2), p. 185). In Japanese Patent JP 95-51764, the reaction of 1-O-acetyl-2,3,4-tri-O-benzyl-L-fucopyranose with polyoxyethylene-30-phytosterol (BPS-30, NIKKO Chem., Japan) under trimethyl-silylbromide/zinc triflate catalysis was described. In Bull. Chem. Soc. 1982, 55(4), pp. 1092–6, 1-O-glycosylations of perbenzyl-sugars under titanium tetrachloride catalysis in dichloromethane are described.

In Liebigs Ann. Org. Bioorg. Chem.; En; 9; 1995; 1673–1680, the production of 3,4,5-trisbenzyloxy-2-benzyloxymethyl-6-(2-hexadecyloxyethoxy)-tetrahydropyran is described. Starting from 2,3,4,6-tetra-O-benzyl-D-glucopyranose, the 1-O-glycosylation is performed with use of $Bu_4NBr$, $CoBr_2$, $Me_3SiBr$ and a molecular sieve in methylene chloride within 60 hours.

A tetrabenzyl derivative, which contains a terminal carboxyl group that is protected as a methyl ester, is described in Carbohydr. Res.; EN; 230; 1; 1992; 117. The carboxyl group can then be released and further reacted. For glycosylation, silver carbonate is used in dichloromethane. The use of expensive silver carbonate limits the batch size and makes an economical up-scaling almost impossible. The same problem applies for the compound below, which was described in Tetrahedron Lett. 30, 44, 1989, p. 6019. Here, 2,3,4,6-tetra-O-benzyl-D-mannosyl-bromide in nitromethane is reacted with 2-benzyloxyethanol with the aid of mercury cyanide to form 1-O-glycoside. The use of mercury cyanide in pilot-plant installations is problematical in nature and can be rejected from the environmental-political standpoint.

The substance libraries for the high-capacity-screening described most recently very frequently use saccharides (Angew. Chemie 1995, 107, 2912). Here, the purpose is to have sugar components present in protected form, which carry a functional group, such as, e.g., —COOH, or —$NH_2$, which can be reacted in, e.g., an automated synthesis. The components, which are used in this respect, were described by Lockhoff, Angew. Chem. 1998, 110 (24), p. 3634. Primarily the 1-O-acetic acid of perbenzyl-glucose is important here. The production is carried out over two stages, via trichloroacetimidate and reaction with hydroxyacetic acid ethyl ester, $BF_3$ catalysis in THF and subsequent saponification with NaOH in MeOH/THF. The total yield over two stages is only 59%, however.

The 1-O-ethyl acetate that has been intermediately processed in this case is obtained in EP 882733 by reaction of 2,3,4,6-tetra-O-benzylglucose with hydroxyacetic acid ethyl ester in the presence of catalytic amounts of p-toluenesulfonic acid by reflux-boiling in benzene, but without data on the yield.

In the same publication, the production of a 1-O-(aminoethyl)-glycoside of the perbenzylated glucose is also described. The reaction is carried out, also starting from trichloroacetimidate, by reaction with N-formylaminoethanol under $BF_3$-catalysis in THF and subsequent saponification in MeOH/THF. The total yield is also relatively low here; it is 45%.

A 1-O-(aminoethyl) derivative of perbenzylxylose passes through as an intermediate product in Carbohydrate Research 1997, 298, p. 173. The synthesis is very lengthy, however, since it starts from 1-bromo-peracetate of xylose. The actual 1-O-glycosylation is carried out via a 1-phenylthioether, which is reacted with 2-azidoethanol under DMTST catalysis (=dimethyl (methylthio)-sulfonium-triflate) in dichloromethane (total number of stages: 7). The total yield is not suitable for an industrial application with less than 40%.

In the survey article by R. R. Schmidt in Angew. Chem. 1986, 98, pp. 213–236, direct reactions of 1-OH-perbenzyl-glucose and -ribose with 2-haloesters and triflates are described. As a base, sodium hydride in THF or benzene is used (Chem. Ber. 1982, 115); the yields are between 40 and 55%. The use of sodium hydride in dioxane or potassium-tert-butylate in THF (both at room temperature) is also described for 1-O-alkylation with triflates (Angew. Chem. 1986, 98, p. 218). The anhydrous reaction conditions that are to be followed most strictly represent a large hurdle in up-scaling such alkylations.

All processes known to date have the great disadvantage that an up-scaling of the process cannot be achieved easily. The use of Lewis acids in 1-O-glycosylation and sodium hydride in 1-O-alkylation already requires anhydrous reaction conditions, which in large batches is always associated with difficulties. The working-up and disposal of reaction adjuvants (Hg/cyanide/etc.) is also a problem in many cases.

The object of the invention was therefore to provide a process with which perbenzylated saccharides with 1-O-functionalized side chains can be produced at a reasonable price and in an ecologically beneficial way on an enlarged scale.

The object of the invention is achieved according to the process indicated in the claims, with which perbenzylated 1-O-glycosides of general formula I

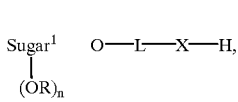

(I)

can be produced. According to the definition of the invention, sugar¹ in general formula I means a monosaccharide functionalized in 1-OH position, whereby in this connection, it can also be a deoxy sugar, which contains an H-atom instead of one or more OH groups. In a preferred embodiment of the invention, the sugar in general formula I means a monosaccharide with 5 or 6 C-atoms, e.g., glucose, mannose, galactose, ribose, arabinose or xylose or deoxy sugars thereof, such as, for example, 6-deoxygalactose (fucose) or 6-deoxy-mannose (rhamnose).

Radical R represents the benzyl group that is present in at least two places based on the monosaccharide that is used or its deoxy form, and is present accordingly in several places with use of di-, tri- or polysaccharides.

Radical X means —O—, —S—, —COO— or —NH—. In the results of the process according to the invention, alcohols, carboxylic acids, or amines of general formula I are thus obtained.

Radical L can mean a straight-chain, branched, saturated, or unsaturated $C_1$–$C_{30}$ carbon chain, which optionally is interrupted by 1–10 oxygen atoms, 1–3 sulfur atoms; 1–2 phenylene groups, 1–2 phenylenoxy groups, 1–2 phenylene-dioxy groups; a thiophene radical, pyrimidine radical or pyridine radical; and/or optionally is substituted with 1–3 phenyl groups, 1–3 carboxy groups, 1–5 hydroxy groups, 1–5 O—$C_1$-$C_7$ alkyl groups, or 1–3 amino groups; 1–3 $CF_3$ groups, or 1–10 fluorine atoms. In terms of the invention, preferred radicals L are

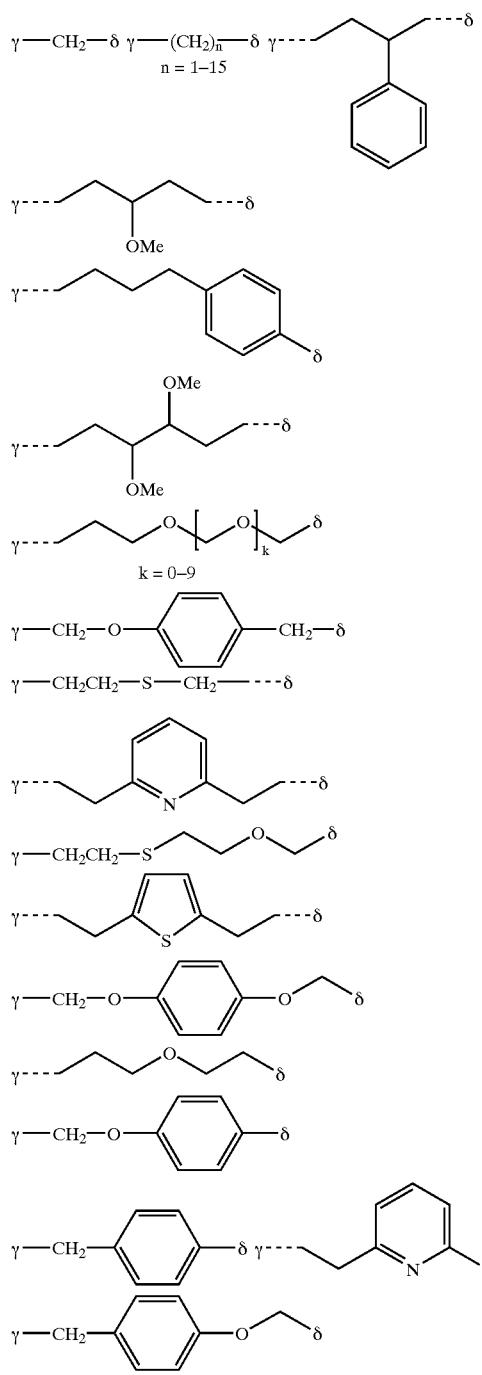

whereby γ means the interface site to the sugar, and δ is the interface site to radical X. An especially preferred linker L is the —$CH_2$— group.

For the production of perbenzylated 1-O-glycosides of general formula I, a perbenzylated 1-OH sugar of general formula II

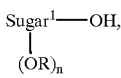

$$\text{Sugar}^1\text{---OH}, \quad (II)$$
$$|$$
$$(OR)_n$$

in which sugar, R and n have the above-indicated meaning, is dissolved in a water-immiscible organic solvent and reacted with an alkylating reagent of general formula III

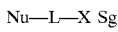

$$\text{Nu---L---X Sg} \quad (III),$$

in which Nu means a nucleofuge, L and X have the above-mentioned meaning, and Sg is a protective group, in the presence of a base and optionally a phase transfer catalyst. As a nucleofuge, for example, the radicals —Cl, —Br, —I, —OTs, —OMs, —OSO$_2$CF$_3$, —OSO$_2$C$_4$F$_9$ or —OSO$_2$C$_8$F$_{17}$ can be contained in the alkylating reagent of general formula III.

Protective group Sg is a common acid- or amine-, hydroxy- or thiol protective group, depending on whether X means the radical —O—, —COO— or —NH—. These protective groups are well known to one skilled in the art (Protective Groups in Organic Syntheses, Second Edition, T. W. Greene and P. G. M. Wuts, John Wiley & Sons, Inc., New York 1991).

The reaction according to the invention can be carried out at temperatures of 0–50° C., preferably 0° C. to room temperature. The reaction times are 10 minutes to 24 hours, preferably 20 minutes to 12 hours.

The base is added either in solid form, preferably fine-powder, or as 10–70%, preferably 30–50%, aqueous solution. NaOH and KOH are used as preferred bases.

As organic, water-immiscible solvents, for example, toluene, benzene, CF$_3$-benzene, hexane, cyclohexane, diethylether, tetrahydrofuran, dichloromethane, MTB or mixtures thereof can be used in the alkylating process according to the invention.

As phase transfer catalysts, the quaternary ammonium or phosphonium salts that are known for this purpose or else crown ethers, such as, e.g., [15]-crown 5 or [18]-crown 6, are used in the process according to the invention. Quaternary ammonium salts with four hydrocarbon groups that are the same or different on the cation, selected from methyl, ethyl, propyl, isopropyl, butyl or isobutyl, are preferably suitable. The hydrocarbon groups on the cation must be large enough to ensure good solubility of the alkylating reagent in the organic solvent. According to the invention, N(butyl)$_4^+$-Cl$^-$, or N(butyl)$_4^+$-HSO$_4^-$, but also N(methyl)$_4$-Cl$^-$ is especially preferably used.

After the reaction is completed, the working-up of the reaction mixture can be carried out by isolation of the still protected end product and subsequent usual cleavage of the protective group to the end product of general formula I. It is preferred, however, not to isolate the still protected end product but rather to remove the solvent, to take up the residue in a new solvent that is suitable for the cleavage of the protective group and to perform the cleavage here. The procedure for cleavage of the protective group and for regeneration of the acid, amino, hydroxy or thiol group is well known to one skilled in the art.

In protective group Sg, e.g., this is an acid protective group, which blocks the acid proton of the carboxy group, thus, e.g., methyl, ethyl, benzyl or tert-butyl, such that the acid is usually regenerated by alkaline hydrolysis. In the process of the invention, for this case after the solvent is removed from the alkylating reaction, the residue is now taken up in a new solvent, e.g., methanol, ethanol, tetrahydrofuran, isopropanol, butanol or dioxane. An aqueous solution is then added to a base, and the alkaline hydrolysis is performed at temperatures of 0–100° C.

As hydroxy protective groups, e.g., benzyl, 4-methoxybenzyl, 4-nitrobenzyl, trityl, diphenylmethyl, trimethylsilyl, dimethyl-tert-butylsilyl, or diphenyl-tert-butylsilyl groups are suitable.

The hydroxy groups can also be present, e.g., as THP-ethers, α-alkoxyethylethers, MEM-ethers or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The hydroxy protective groups can be released according to the literature methods that are known to one skilled in the art, e.g., by hydrogenolysis, acid treatment of ethers and ketals, alkali treatment of esters or treatment of silyl protective groups with fluoride (see, e.g., Protective Groups in Organic Syntheses, Second Edition, T. W. Greene and P. G. M. Wuts, John Wiley & Sons, Inc., New York, 1991).

The thiol groups can be protected as benzyl-ethers, which can be cleaved with sodium in ammonia or boiling ethanol (W. J. Patterson, v. du Vigneaud, J. Biol. Chem. 111:393, 1993). S-tert-Butyl ethers can be easily cleaved with hydrogen fluoride/anisole at room temperature [S. Salzakibona et al., Bull. Chem. Soc. Japn, 40:2164, (1967)]. S-Benzyloxycarbonyl derivatives can be easily cleaved by concentrated ammonia solution at room temperature (A. Berger et al., J. Am. Chem. Soc., 78:4483, 1956). S-Benzyloxycarbonyl derivatives of trifluoroacetic acid are cleaved only at boiling point [L. Zervas et al., J. Am. Chem. Soc., 85:1337 (1963)].

The NH$_2$ groups can be protected and released again in a variety of ways. The N-trifluoroacetyl derivative is cleaved by potassium or sodium carbonate in water [H. Newman, J. Org. Chem., 30:287 (1965), M. A. Schwartz et al., J. Am. Chem. Soc., 95 G12 (1973)] or simply by ammonia solution [M. Imazama and F. Eckstein, J. Org. Chem., 44:2039 (1979)]. The tert-butyloxycarbonyl derivative is equally easy to cleave: stirring with trifluoroacetic acid suffices [B. F. Lundt et al., J. Org. Chem., 43:2285 (1978)]. The group of NH$_2$-protective groups to be cleaved hydrogenolytically or reductively is very large: The N-benzyl group can be cleaved easily with hydrogen/Pd—C [W. H. Hartung and R. Simonoff, Org. Reactions VII, 263 (1953)], which also applies for the trityl group [L. Zervas, et al., J. Am. Chem. Soc., 78:1359 (1956)] and the benzyloxycarbonyl group [M. Bergmann and L. Zervas Ber. 65:1192 (1932)].

Of the silyl derivatives, the easily cleavable tert-butyldiphenylsilyl compounds [L. E. Overman et al., Tetrahedron Lett., 27:4391 (1986)] and the 2-(trimethylsilyl)-ethyl carbamate [L. Grehn et al., Angew. Chem. Int. Ed. Engl., 23:296 (1983)] and the 2-trimethylsilylethanesulfonamide [R. S. Garigipati and S. M. Weinreb, J. Org. Chem., 53:4134 (1988)] are used, which can be cleaved with fluoride ions. Especially easily cleavable is the 9-fluorenylmethyl-carbamate: The cleavage is carried out with amines such as piperidine, morpholine, 4-dimethylaminopyridine, but also with tetrabutylammonium fluoride [L. A. Corpino et al., J. Org. Chem., S5:1673 (1990); M. Ueki and M. Amemiya, Tetrahedron Lett., 28:6617 (1987)].

The isolation of the end product of general formula I (alcohol, thiol, amine or carboxylic acid) that is obtained is also carried out according to common methods that are well known to one skilled in the art.

Thus, for example, in the case of the acid protective group, the solvent is evaporated from the hydrolysis reaction, and the residue is taken up in an aprotic solvent.

By acidification with an aqueous acid solution, the pH is set at about 2–4, and then the organic phase is separated. Using crystallization or chromatography, the perbenzylated 1-O-glycoside can now be obtained.

The compounds of general formula I that are obtained optionally also can be converted into their salts in the usual way.

The yields of the compounds of general formula I, which can be achieved with the process according to the invention, are good. For known compounds in which a comparison with the prior art is possible, they exceed the yields of the prior art. Thus, for example, for 1-O-acetic acid of perbenzylated glucose, a total yield of 59% is described in Angew. Chem. 1998, 110 (24), p. 3634 with the process that is mentioned there, while according to the invention, the yield for this compound is 82% over two stages (cf. Example 7 of this application). The production of the compound of Example 12 of this application is also described in this publication. While the yield of this compound according to the invention is 78% over 2 stages, only 45% is achieved with the process that is described in the publication.

In addition to the high yields, the process according to the invention also offers the advantage that it starts from economical starting materials, makes possible a scale-up of the process, and allows an easy isolation of the end products.

The starting materials are commercially available products or can be obtained easily from commercially available precursors. Tetra-2,3,4,6-O-benzyl-D-glucopyranose thus can be obtained in the case of Fluka AG, Duchs, Switzerland. In the case of Fluka, methyl-D-manno-pyranoside and methyl-D-galactopyranoside are also catalog items. By benzylation and cleavage of the glycoside, 2,3,4,6-tetra-O-benzyl-D-mannose or -galactose can be obtained.

The perbenzyl-1-OH derivatives of the pentoses (ribose, arabinose), hexoses and deoxyhexoses (rhamnose, fucose) can be obtained via the sequence of methylglycoside-perbenzyl-methylglycoside-perbenzyl-1-OH-saccharide.

The compounds that are produced according to the invention are valuable intermediate products in synthetic chemistry. They can thus be used, for example, in the synthesis of carbohydrate dendrimers, for synthesis of NMR contrast media and for introducing sugar radicals into pharmaceutical agents.

The process according to the invention is to be explained in more detail below in the embodiments.

EXAMPLE 1
2,3,4,6-Tetra-O-benzyl-1-O-carboxymethyl-mannopyranose

A mixture that consists of 54.1 g (100 mmol) of 2,3,4,6-tetra-O-benzyl-mannopyranose, 1.70 g (5 mmol) of tetrabutylammonium hydrogen sulfate and 33.7 g (600 mmol) of fine-powder potassium hydroxide in 350 ml of toluene is cooled to 0° C. At 0° C. 29.3 g (150 mmol) of bromoacetic acid tert-butyl ester is added in drops over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is taken up in 500 ml of ethanol. 40 ml of 50% aqueous sodium hydroxide solution is added, and it is refluxed for 0.5 hour. It is cooled to 0° C., set at pH 8 with 10% aqueous hydrochloric acid, and then the solvent is distilled off (vacuum). The residue is taken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/nhexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 50.9 g (85% of theory, over 2 stages) of a colorless, viscous oil

| Elementary analysis: | | |
|---|---|---|
| Cld: | C 72.22 | H 6.40 |
| Fnd: | C 72.38 | H 6.55 |

EXAMPLE 2
2,3,4,6-Tetra-O-benzyl-1-O-carboxymethyl-mannopyranose

A mixture that consists of 54.1 g (100 mmol) of 2,3,4,6-tetra-O-benzyl-mannopyranose, 1.7 g (5 mmol) of tetrabutylammonium hydrogen sulfate and 24 g (600 mmol) of fine-powder sodium hydroxide in 350 ml of toluene is cooled to 0° C. At 0° C., 29.3 g (150 mmol) of bromoacetic acid ethyl ester is added in drops over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is taken up in 500 ml of ethanol/50 ml of water. 60 ml of 50% aqueous sodium hydroxide solution is added, and it is refluxed for four hours. It is cooled to 0° C., set at pH 8 with 10% aqueous hydrochloric acid, and the solvent is distilled off (vacuum). The residue is taken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n=hexane/ethanol/acetic acid=20:5:3:0.5). The product-containing fractions are evaporated, dissolved in 400 ml of ethyl acetate, and shaken out three times with 200 ml of water. Then, the organic phase is separated and evaporated to the dry state in a vacuum.

Yield: 48.5 g (81% of theory, over two stages) of a colorless, viscous oil

| Elementary analysis: | | |
|---|---|---|
| Cld: | C 72.22 | H 6.40 |
| Fnd: | C 72.41 | H 6.16 |

EXAMPLE 3
2,3,4,6-Tetra-O-benzyl-1-O-carboxymethyl-mannopyranose

A mixture that consists of 54.1 g (100 mmol) of 2,3,4,6-tetra-O-benzyl-mannopyranose, 0.55 g (5 mmol) of tetramethylammonium chloride and 33.7 g (600 mmol) of fine-powder potassium hydroxide in 350 ml of benzene is cooled to 10° C. At 10° C., 35.7 g (160 mmol) of 6-bromohexanoic acid ethyl ester is added in drops over 10 minutes while being stirred vigorously. It is stirred for 2 hours at 10° C. 250 ml of MTB (methyl-tert-butyl ether) is added, solid is filtered out, and the filtrate is evaporated to the dry state in a vacuum. The residue is taken up in 500 ml of ethanol/50 ml of water. 60 ml of 50% aqueous sodium hydroxide solution is added, and it is refluxed for four hours. It is cooled to 0° C., set at pH 8 with 10% aqueous hydrochloric acid, and then the solvent is distilled off (vacuum). The residue is taken up in 300 ml of water, 500 ml of ethyl acetate is added, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate, and shaken out three times with 200 ml of water. Then, the organic phase is separated and evaporated to the dry state in a vacuum.

Yield: 51.7 g (79% of theory, over two stages) of a colorless solid

| Elementary analysis: | | |
|---|---|---|
| Cld: | C 73.37 | H 7.08 |
| Fnd: | C 73.50 | H 7.27 |

EXAMPLE 4

2,3,4,6-Tetra-O-benzyl-1-O-(1-phenyl-1-carboxy-eth-2-yl)-mannopyranose A mixture that consists of 54.1 g (100 mmol) of 2,3,4,6-tetra-O-benzyl-mannopyranose, 1.39 g (5 mmol) of tetrabutylammonium chloride and 24 g (600 mmol) of fine-powder sodium hydroxide in 350 ml of toluene is cooled to 0° C. At 0° C., 38.6 g (150 mmol) of 2-phenyl-3-bromopropionic acid-ethyl ester is added in drops and dissolved in 30 ml of toluene over 10 minutes while being stirred vigorously. It is stirred for one hour at 0° C. 250 ml of MTB (methyl-tert-butyl ether) is added, solid is filtered out, and the filtrate is evaporated to the dry state in a vacuum. The residue is taken up in 500 ml of ethanol/50 ml of water. 60 ml of 50% aqueous sodium hydroxide solution is added, and it is refluxed for four hours. It is cooled to 0° C., set at pH 8 with 10% aqueous hydrochloric acid, and then the solvent is distilled off (vacuum). The residue is taken up in 300 ml of water and 500 ml of ethyl acetate, and the pH of the sequence phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 54.5 g (79% of theory, over two stages) of a colorless solid

| Elementary analysis: | | |
|---|---|---|
| Cld: | C 74.98 | H 6.44 |
| Fnd: | C 75.11 | H 6.58 |

EXAMPLE 5

2,3,4,6-Tetra-O-benzyl-1-O-carboxymethyl-mannopyranose

A mixture that consists of 54.1 g (100 mmol) of 2,3,4,6-tetra-O-benzyl-mannopyranose, 1.39 g (5 mmol) of tetrabutylammonium chloride in 350 ml of toluene and 150 ml of 50% aqueous potassium hydroxide solution is cooled to 0° C. At 0° C., 30.12 g (200 mmol) of chloroacetic acid-tert-butyl ester is added in drops over 20 minutes while being stirred vigorously. It is stirred for one hour at 10° C. 250 ml of methyl-tert-butyl ether is added, the organic phase is separated, and the aqueous phase is extracted twice with 250 ml of water. The solvent of the combined organic phases is distilled off in a vacuum, and the residue is taken up in 500 ml of ethanol. 40 ml of 50% aqueous sodium hydroxide solution is added, and it is refluxed for 0.5 hour. It is cooled to 0° C., set at pH 8 with 10% aqueous hydrochloric acid, and then the solvent is distilled off (vacuum). The residue is taken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 41.1 g (82% of theory, over two stages) of a colorless, viscous oil

| Elementary analysis: | | |
|---|---|---|
| Cld: | C 72.22 | H 6.40 |
| Fnd: | C 72.01 | H 6.63 |

EXAMPLE 6

2,3,4,6-Tetra-O-benzyl-1-O-carboxymethyl-glucopyranose

A mixture that consists of 54.1 g (100 mmol) of 2,3,4,6-tetra-O-benzyl-glucopyranose, 1.39 g (5 mmol) of tetrabutylammonium chloride and 24 g (600 mmol) of fine-powder sodium hydroxide in 300 ml of tetrahydrofuran is cooled to 0° C. At 0° C., 78 g (150 mmol) of 5-tosyloxy-pentanecarboxylic acid-tert-butyl ester, dissolved in 40 ml of tetrahydrofuran, is added in drops over 30 minutes while being stirred vigorously. It is stirred for 3 hours at 0° C. 300 ml of MTB (methyl-tert-butyl ether) is added, solid is filtered out, and the filtrate is evaporated to the dry state in a vacuum. The residue is taken up in 500 ml of methanol. 50 ml of 50% aqueous sodium hydroxide solution is added, and it is refluxed for one hour. It is cooled to 0° C., set at pH 8 with 10% aqueous hydrochloric acid, and then the solvent is distilled off (vacuum). The residue is taken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of dichloromethane. The combined organic phases are dried on magnesium sulfate, the solvent is distilled off in a vacuum, and the residue is chromatographed on silica gel (mobile solvent: dichloromethane/n-hexane/ethanol/acetic acid= 20:5:3:0.5). The product-containing fractions are concentrated by evaporation, dissolved in 400 ml of ethyl acetate, and shaken out three times with 200 ml of water. Then, the organic phase is separated and evaporated to the dry state in a vacuum.

Yield: 50 g (78% of theory, over two stages) of a colorless solid

| Elementary analysis: | | |
| --- | --- | --- |
| Cld: | C 73.10 | H 6.92 |
| Fnd: | C 73.21 | H 7.09 |

EXAMPLE 7
2,3,4,6-Tetra-O-benzyl-1-O-carboxymethyl-glucopyranose

A mixture that consists of 54.1 g (100 mmol) of 2,3,4,6-tetra-O-benzyl-glucopyranose, 1.39 g (5 mmol) of tetrabutylammonium chloride in 350 ml of toluene and 200 ml of 50% aqueous sodium hydroxide solution is cooled to 0° C. At 0° C., 29.3 g (150 mmol) of bromoacetic acid-tert-butyl ester is added in drops over 20 minutes while being stirred vigorously. It is stirred for 0.5 hour at 0° C. 250 toluene is added, the organic phase is separated, and the aqueous phase is extracted twice with 150 ml of toluene. The solvent of the combined organic phases is distilled off in a vacuum, and the residue is taken up in 400 ml of methanol. 50 ml of 50% aqueous sodium hydroxide solution is added, and it is refluxed for 0.5 hour. It is cooled to 0° C., set at pH 8 with 10% aqueous hydrochloric acid, and then the solvent is distilled off (vacuum). The residue is taken up in 300 ml of water and 500 ml of dichloromethane, and the pH of the aqueous phase is set at 2 while being stirred (10% aqueous hydrochloric acid). The organic phase is separated, and the aqueous phase is extracted once more with 200 ml of dichloromethane. The combined organic phases are dried on magnesium sulfate, the solvent is distilled off in a vacuum, and the residue is chromatographed on silica gel (mobile solvent: dichloromethane/n-hexane/ethanol/acetic acid= 20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 49.1 g (82% of theory, over two stages) of a colorless, viscous oil

| Elementary analysis: | | |
| --- | --- | --- |
| Cld: | C 72.22 | H 6.40 |
| Fnd: | C 72.09 | H 6.59 |

EXAMPLE 8
2,3,4,6-Tetra-O-benzyl-1-O-carboxymethyl-glucopyranose

A mixture that consists of 54.1 g (100 mmol) of 2,3,4,6-tetra-O-benzyl-glucopyranose, 0.55 g (5 mmol) of tetramethylammonium chloride and 33.7 g (600 mmol) of fine-powder potassium hydroxide in 350 ml of benzene is cooled to 0° C. At 0° C., 44 g (150 mmol) of 11-bromoundecanoic acid-ethyl ester, dissolved in 50 ml of benzene, is added in drops over 30 minutes while being stirred vigorously. It is stirred for two hours at 20° C. 250 ml of methyl-tert-butyl ether is added, solid is filtered out, and the filtrate is evaporated to the dry state in a vacuum. The residue is taken up in 500 ml of ethanol/50 ml of water. 60 ml of 50% aqueous sodium hydroxide solution is added, and it is refluxed for five hours. It is cooled to 0° C., set at pH 8 with 10% aqueous hydrochloric acid, and then the solvent is distilled off (vacuum). The residue is taken up in 300 ml of water and 500 ml of dichloromethane, and the pH of the aqueous phase is set at 2 while being stirred (10% aqueous hydrochloric acid). The organic phase is separated, and the aqueous phase is extracted once more with 200 ml of dichloromethane. The combined organic phases are dried on magnesium sulfate, the solvent is distilled off in a vacuum, and the residue is chromatographed on silica gel (mobile solvent: dichloromethane/n-hexane/ethanol/acetic acid= 20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 58.4 g (78% of theory, over two stages) of a colorless solid

| Elementary analysis: | | |
| --- | --- | --- |
| Cld: | C 75.37 | H 7.54 |
| Fnd: | C 75.52 | H 7.73 |

EXAMPLE 9
2,3,4, 6Tetra-O-benzyl-1-O-carboxymethyl-galactopyranose

A mixture that consists of 54.1 g (100 mmol) of 2,3,4,6-tetra-O-benzyl-mannopyranose, 1.39 g (5 mmol) of tetrabutylammonium chloride in 350 ml of toluene and 150 ml of 50% aqueous potassium hydroxide solution is cooled to 0° C. At 0° C., 30.12 g (200 mmol) of chloroacetic acid-tert-butyl ester is added in drops over 20 minutes while being stirred vigorously. It is stirred for one hour at 10° C. 250 ml of methyl-tert-butyl ether is added, the organic phase is separated, and the aqueous phase is extracted twice with 250 ml of water. The solvent of the combined organic phases is distilled off in a vacuum, and the residue is taken up in 500 ml of ethanol. 40 ml of 50% aqueous sodium hydroxide solution is added, and it is refluxed for 0.5 hour. It is cooled to 0° C., set at pH 8 with 10% aqueous hydrochloric acid, and then, the solvent is distilled off (vacuum). The residue is shaken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n-hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 41.1 g (82% of theory, over two stages) of a colorless, viscous oil

| Elementary analysis: | | |
|---|---|---|
| Cld: | C 72.22 | H 6.40 |
| Fnd: | C 72.03 | H 6.63 |

EXAMPLE 10
2,3,4,6-Tetra-O-benzyl-1-O-[1-(4-carboxy)-phenyl-prop-3-yl-galactopyranose A mixture that consists of 54.1 g (100 mmol) of 2,3,4,6-tetra-O-benzyl-galactopyranose, 1.39 g (5 mmol) of tetrabutylammonium chloride and 24 g (600 mmol) of fine-powder sodium hydroxide in 300 ml of tetrahydrofuran is cooled to 10° C. At 10° C., 43 g (150 mmol) of 4-(3-methanesulfonyloxy-propyl)-benzoic acid-ethyl ester, dissolved in 50 ml of tetrahydrofuran, is added in drops over 30 minutes while being stirred vigorously. It is stirred for two hours at 100° C. 300 ml of MTB (methyl-tert-butyl ether) is added, solid is filtered out, and the filtrate is evaporated to the dry state in a vacuum. The residue is taken up in 500 ml of methanol/50 ml of water. 60 ml of 50% aqueous sodium hydroxide solution is added, and it is refluxed for five hours. It is cooled to 0° C., set at pH 8 with 10% aqueous hydrochloric acid, and then the solvent is distilled off (vacuum). The residue is taken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n=hexane/ethanol/acetic acid=20:5:3:0.5). The product-containing fractions are concentrated by evaporation, dissolved in 400 ml of ethyl acetate and shaken out three times with 200 ml of water. Then, the organic phase is separated and evaporated to the dry state in a vacuum.

Yield: 54.1 g (77% of theory, over two stages) of a colorless solid

| Elementary analysis: | | |
|---|---|---|
| Cld: | C 75.19 | H 6.60 |
| Fnd.: | C 75.02 | H 6.79 |

EXAMPLE 11
2,3,5-Tri-O-benzyl-1-O-carboxymethyl-ribofuranose

A mixture that consists of 42.1 g (100 mmol) of 2,3,5-tri-O-ribofuranose, 1.39 g (5 mmol) of tetrabutylammonium chloride in 350 ml of toluene and 200 ml of 50% aqueous sodium hydroxide solution is cooled to 0° C. At 0° C., 29.3 g (150 mmol) of bromoacetic acid-tert-butyl ester is added in drops over 20 minutes while being stirred vigorously. It is stirred for one hour at 0° C. 250 ml of methyl-tert-butyl ether is added, the organic phase is separated, and the aqueous phase is extracted twice with 200 ml of methyl-tert-butyl ether. The solvent of the combined organic phases is distilled off in a vacuum, and the residue is taken up in 500 ml of ethanol. 50 ml of 50% aqueous sodium hydroxide solution is added, and it is refluxed for 0.5 hour. It is cooled to 0° C., set at pH 8 with 10% aqueous hydrochloric acid, and then the solvent is distilled off (vacuum). The residue is taken up in 300 ml of water and 500 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/nhexane/ethanol/acetic acid=20:5:3:0.5). The product-containing fractions are concentrated by evaporation, dissolved in 200 ml of ethyl acetate and shaken out three times with 200 ml of water. Then, the organic phase is separated and evaporated to the dry state in a vacuum.

Yield: 39.2 g (82% of theory, over two stages) of a colorless, viscous oil

| Elementary analysis: | | |
|---|---|---|
| Cld: | C 70.28 | H 6.32 |
| Fnd: | C 70.11 | H 6.51 |

EXAMPLE 12
2,3,5-Tri-O-benzyl-1-O-(1-amino-eth-2-yl)-ribofuranose

A mixture that consists of 42.1 g (100 mmol) of 2,3,5-tri-O-benzyl-ribofuranose, 3.40 g (10 mmol) of tetrabutylammonium hydrogen sulfate and 33.7 g (600 mmol) of fine-powder potassium hydroxide in 3050 ml of benzene is cooled to 10° C. At 10° C., 38.1 g (150 mmol) of N-(2-bromoethyl)-phthalimide, dissolved in 100 ml of benzene, is added in drops over 40 minutes while being stirred vigorously. It is stirred for three hours at 10° C. 300 ml of benzene is added, solid is filtered out, and the filtrate is evaporated to the dry state in a vacuum. The filtrate residue is dissolved in 500 ml of ethanol, 25.03 g of hydrazine hydrate (500 mmol) is added, and it is refluxed for six hours. It is allowed to cool to 0° C., deposited precipitate is filtered out, and the filtrate is evaporated to the dry state in a vacuum. The residue is dissolved in 400 ml of dichloromethane, and this solution is washed twice with 5% aqueous sodium hydroxide solution and then once with water (in each case 300 ml). The organic phase is evaporated to the dry state in a vacuum, and the residue is chromatographed on silica gel (mobile solvent: dichloromethane/ethanol/triethylamine=20:2:0.1).

Yield: 36.2 g (78% of theory, over two stages) of a colorless solid

| Elementary analysis: | | | |
|---|---|---|---|
| Cld: | C 72.55 | H 7.17 | N 3.02 |
| Fnd: | C 72.39 | H 7.38 | N 2.87 |

EXAMPLE 13
2,3,4,6-Tetra-O-benzyl-1-O-(1-amino-prop-3-yl)-galactopyranose

A mixture that consists of 42.1 g (100 mmol) of 2,3,4,6-tetra-O-benzyl-galactopyranose, 1.7 g (5 mmol) of tetrabutylammonium hydrogen sulfate and 33.7 g (600 mmol) of fine-powder potassium hydroxide in 350 ml of benzene is cooled to 10° C. At 10° C., 40.2 g (150 mmol) of N-(3-bromopropyl)-phthalimide, dissolved in 100 ml of benzene, is added in drops over 40 minutes while being stirred vigorously. It is stirred for three hours at 10° C. 300 ml of benzene is added, solid is filtered out, and the filtrate is evaporated to the dry state in a vacuum. The filtrate residue is dissolved in 500 ml of ethanol, 25.03 ml of hydrazine hydrate (500 mmol) is added, and it is refluxed for six hours. It is allowed to cool to 0° C., deposited precipitate is filtered out, and the filtrate is evaporated to the dry state in a vacuum. The residue is dissolved in 400 ml of dichloromethane, this solution is washed twice with 5% aqueous sodium hydroxide solution, then once with water (in each case 300 ml). The organic phase is evaporated to the dry state in a vacuum, and the residue is chromatographed on silica gel (mobile solvent: dichloromethane/ethanol/triethylamine=20:2:0.1).

Yield: 46 g (77% of theory, over two stages) of a colorless solid

| Elementary analysis: | | | |
|---|---|---|---|
| Cld: | C 74.35 | H 7.25 | N 2.34 |
| Fnd: | C 74.24 | H 7.41 | N 2.27 |

EXAMPLE 14
2,3,4,6-Tetra-O-benzyl-1-O-(1-amino-hex-6-yl)-mannopyranose

A mixture that consists of 54.1 g (100 mmol) of 2,3,4,6-tetra-O-benzyl-mannopyranose, 1.39 g (5 mmol) of tetrabutylammonium chloride in 350 ml of dichloromethane and 200 ml of 60% aqueous potassium hydroxide solution is cooled to 0° C. At 0° C., 60.3 g (150 mmol) of 6-bromohexylamine-N-(9-fluorenylmethoxy-carbonyl) is added in drops over 30 minutes while being stirred vigorously. It is stirred for one hour at 0° C. 300 ml of dichloromethane is added, the organic phase is separated, and the aqueous phase is extracted twice with 200 ml of dichloromethane. The solvent of the combined organic phases is distilled off in a vacuum. The residue is taken up in 250 ml of ethanol, and 100 g (1.17 mol) of piperidine is added. It is stirred for five hours at 40° C. The solution is evaporated to the dry state, and the residue is chromatographed on silica gel (mobile solvent: dichloromethane/ethanol/triethylamine=20:2:0.1).

Yield: 41.1 g (79% of theory, over two stages) of a colorless solid

| Elementary analysis: | | | |
|---|---|---|---|
| Cld: | C 69.33 | H 9.50 | N 2.70 |
| Fnd: | C 69.44 | H 9.68 | N 2.54 |

EXAMPLE 15
2,3,4-Tri-O-benzyl-6-deoxy-1-O-(1-amino-but-4-yl)-fucopyranose

A mixture that consists of 43.5 g (100 mmol) of 2,3,4-tri-O-benzyl-6-deoxy-fucopyranose, 1.7 g (5 mmol) of tetrabutylammonium hydrogen sulfate in 350 ml of dichloromethane and 200 ml of 60% aqueous sodium hydroxide solution is cooled to 0° C. At 10° C., 47.4 g (150 mmol) of 2-(trimethylsilyl)-ethylsulfonic acid-N-(4-bromobutyl)-amide, dissolved in 100 ml of dichloromethane, is added in drops over 30 minutes while being stirred vigorously. It is stirred for two hours at 10° C. 300 ml of dichloromethane is added, the organic phase is separated, and the aqueous phase is extracted twice with 200 ml of dichloromethane. The solvent of the combined organic phases is distilled off in a vacuum. The residue is taken up in 350 ml of acetonitrile, and 52.3 g (200 mmol) of tetrabutylammonium fluoride is added as a monohydrate. It is stirred for three hours at 50° C. The solution is evaporated to the dry state, and the residue is chromatographed on silica gel (mobile solvent: dichloromethane/ethanol/triethylamine=20:2:0.1).

Yield: 39.4 g (78% of theory, over two stages) of a colorless solid

| Elementary analysis: | | | |
|---|---|---|---|
| Cld: | C 73.64 | H 7.77 | N 2.77 |
| Fnd: | C 73.53 | H 7.91 | N 2.65 |

EXAMPLE 16
2,3,4,6-Tetra-O-benzyl-1-O-(3,6,9,12,15-pentaoxa-1-carboxy-hexadec-16-yl)-glucopyranose A mixture that consists of 54.1 g (100 mmol) of 2,3,4,6-tetra-O-benzyl-glucopyranose, 1.39 g (5 mmol) of tetrabutylammonium chloride and 24 g (600 mmol) of fine-powder sodium hydroxide in 350 ml of toluene is cooled to 0° C. At 0° C., 64.3 g (130 mmol) of 17-tosyloxy-3,6,9,12,15-pentaoxaheptadecanoic acid-ethyl ester, dissolved in 100 ml of tetrahydrofuran, is added in drops over 50 minutes while being stirred vigorously. It is stirred for three hours at 0° C. 300 ml of dichloromethane is added, solid is filtered out, and the filtrate is evaporated to the dry state in a vacuum. The residue is taken up in 500 ml of ethanol/100 ml of water. 60 ml of 60% aqueous sodium hydroxide solution is added, and it is refluxed for five hours. It is cooled to 0° C., set at pH 8 with 10% aqueous hydrochloric acid, and then the solvent is distilled off (vacuum). The residue is taken up in 300 ml of water and 400 ml of ethyl acetate, and the pH of the aqueous phase is set at 2 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/n hexane/ethanol/acetic acid=20:3:5:0.5). The product-containing fractions are concentrated by evaporation, dissolved in 400 ml of ethyl acetate, and shaken out three times with 200 ml of water. Then, the organic phase is separated and evaporated to the dry state in a vacuum.

Yield: 64.3 g (77% of theory, over two stages) of a colorless oil

| Elementary analysis: | | |
|---|---|---|
| Cld: | C 66.17 | H 7.00 |
| Fnd: | C 66.03 | H 7.19 |

EXAMPLE 17
2,3,4, 6-Tetra-O-benzyl-1-O- (1-hydroxy-eth-2-yl)-mannopyranose

A mixture that consists of 54.1 g (100 mmol) of 2,3,4,6-tetra-O-benzyl-mannopyranose, 1.7 g (5 mmol) of tetrabutylammonium hydrogen sulfate and 33.7 g (600 mmol) of fine-powder potassium hydroxide in 350 ml of benzene is cooled to 0° C. At 0° C., 31.4 g (150 mmol) of 2,2-dimethyl-propionic acid-bromoethylester is added in drops over 30 minutes while being stirred vigorously. It is stirred for two hours at 0° C. 300 ml of benzene is added, solid is filtered out, and the filtrate is evaporated to the dry state in a vacuum. The residue is taken up in 500 ml of ethanol/100 ml of water. 100 ml of 50% aqueous potassium hydroxide solution is added, and it is refluxed for eight hours. It is cooled to 0° C., set at pH 8 with 10% aqueous hydrochloric acid, and then the solvent is distilled off (vacuum). The residue is taken up in 300 ml of water and 400 ml of ethyl acetate, and the pH of the aqueous phase is set at 5 while being stirred (10% aqueous hydrochloric acid). The organic phase is separated, and the aqueous phase is extracted once more with 200 ml of ethyl acetate. The combined organic phases are dried on magnesium sulfate, the solvent is distilled off in a vacuum, and the residue is chromatographed on silica gel (mobile solvent: dichloromethane/nhexane/ethanol=20:8:2). The product-containing fractions are concentrated by evaporation.

Yield: 45.6 g (78% of theory, over two stages) of a colorless, viscous oil

| Elementary analysis: | | |
|---|---|---|
| Cld: | C 73.95 | H 6.90 |
| Fnd: | C 73.84 | H 7.03 |

EXAMPLE 18
2,3,4,6-Tetra-O-benzyl-1-O-(1-hydroxy-hex-6-yl)-glucopyranose

A mixture that consists of 54.1 g (100 mmol) of 2,3,4,6-tetra-O-benzylglucopyranose, 1.39 g (5 mmol) of tetrabutylammonium chloride and 24 g (600 mmol) of fine-powder sodium hydroxide in 350 ml of dichloromethane is cooled to 10° C. At 10° C., 41.3 g (140 mmol) of 1-(dimethyl-tert-butylsilyloxy)-6-bromohexane, dissolved in 100 ml of dichloromethane, is added in drops over 50 minutes while being stirred vigorously. It is stirred for three hours at 10° C. 350 ml of dichloromethane is added, solid is filtered out, and the filtrate is evaporated to the dry state in a vacuum. The residue is taken up in 350 ml of acetonitrile, and 52.3 g (200 ml) of tetrabutylammonium fluoride is added (as a monohydrate). It is stirred for three hours at 50° C. The solution is evaporated to the dry state, and the residue is chromatographed on silica gel (mobile solvent: dichloromethane/ethanol=20:1).

Yield: 49.3 g (77% of theory, over two stages) of a colorless solid

| Elementary analysis: | | |
|---|---|---|
| Cld: | C 74.97 | H 7.55 |
| Fnd: | C 74.83 | H 7.74 |

EXAMPLE 19
2,3,4,6-Tetra-O-benzyl-1-O-(1-hydroxy-eth-2-yl)-galactopyranose

A mixture that consists of 54.1 g (100 mmol) of 2,3,4,6-tetra-O-benzyl-benzylgalactopyranose, 1.64 g (15 mmol) of tetramethylammonium chloride in 350 ml of toluene and 200 ml of 60% aqueous sodium hydroxide solution is cooled to 0° C. At 0° C., 52.7 g (130 mmol) of 2-(4,4'-dimethoxytriphenylmethyloxy)-ethylbromide, dissolved in 100 ml of toluene, is added in drops over 30 minutes while being stirred vigorously. It is stirred for three hours at 0° C. 300 ml of toluene is added, the organic phase is separated, and the aqueous phase is extracted twice with 200 ml of toluene. The solvent is distilled off in a vacuum. The residue is taken up in 500 ml of dichloromethane, and 25 g (194 mmol) of dichloroacetic acid is added. It is stirred for three hours at 35° C. The solution is washed three times with 300 ml of 10% aqueous sodium hydroxide solution, and the organic phase is evaporated to the dry state, and the residue is chromatographed on silica gel (mobile solvent: dichloromethane/ethanol=20:1).

Yield: 46.2 g (79% of theory, over two stages) of a colorless, viscous oil

| Elementary analysis: | | |
|---|---|---|
| Cld: | C 73.95 | H 6.90 |
| Fnd: | C 73.87 | H 7.05 |

EXAMPLE 20
2,3,4-Tri-O-benzyl-6-deoxy-1-O-(1-hydroxy-3,6,9,12-tetraaza-tetradec-14-yl)-galactopyranose A mixture that consists of 43.5 g (100 mmol) of 2,3,4-tri-O-benzyl-6-deoxygalactopyranose, 1.39 g (5 mmol) of tetrabutylammonium chloride and 24 g (600 mmol) of fine-powder sodium hydroxide in 350 ml of tetrahydrofuran is cooled to 0° C. At 0° C., 66.1 g (130 mmol) of 14-tosyloxy-3,6,9,12-tetraaza-1-(dimethyl-tert-butylsilyloxy)-tetradecane, dissolved in 100 ml of tetrahydrofuran, is added in drops over 40 minutes while being stirred vigorously. It is stirred for three hours at 10° C. 300 ml of dichloromethane is added, solid is filtered out, and the filtrate is evaporated to the dry state in a vacuum. The residue is taken up in 350 ml of acetonitrile, and 52.3 g (200 ml) of tetrabutylammonium fluoride is added as a monohydrate. It is stirred for three hours at 50° C. The solution is evaporated to the dry state, and the residue is chromatographed on silica gel (mobile solvent: dichloromethane/ethanol=20:1).

Yield: 51.1 g (78% of theory, over two stages) of a colorless, viscous oil

| Elementary analysis: | | |
|---|---|---|
| Cld: | C 67.87 | H 7.70 |
| Fnd: | C 68.01 | H 7.91 |

What is claimed is:
1. A process for the production of perbenzylated 1-O-glycosides of formula I

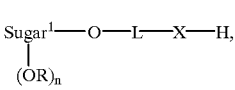

of a salt thereof,
in which
   $sugar^1$ is a monosaccharide that is functionalized in 1-OH- position,
   R represents benzyl,
   n means 2, 3 or 4,
   X means —S—, —COO— or —NH—
and
   L means a straight-chain, branched, saturated or unsaturated $C_1$–$C_{30}$ carbon chain, which optionally is interrupted by 1–10 oxygen atoms, 1–3 sulfur atoms, 1–2 phenylene groups, 1–2 phenylenoxy groups, 1–2 phenylenedioxy groups, a thiophene radical, pyrimidine radical or pyridine radical, and/or optionally is substituted with 1–3 phenyl groups, 1–3 carboxyl groups, 1–5 hydroxy groups, 1–5 O—$C_1$–$C_7$ alkyl groups, 1–3 amino groups, 1–3 $CF_3$ groups or 1–10 fluorine atoms comprising reacting a perbenzylated 1-OH-sugar of formula II

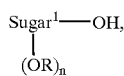

(II)

in which sugar$^1$, R and n have the indicated meaning, with an alkylating reagent of formula (III)

Nu—L—X—Sg    (III), in which Nu means a nucleofuge, L and X have the abovementioned meaning, and Sg represents a protective group, in an organic solvent in the presence of a base and optionally a phase transfer catalyst at a temperature of 0–50° C., cleaving the protective group, and optionally converting reaction product obtained into a salt.

2. The process according to claim 1, wherein a perbenzylated monosaccharide with 5 to 6 C-atoms or a deoxy compound thereof is used as a per benzylated 1-OH-sugar of formula II.

3. The process according to claim 1, wherein perbenzylated glucose, mannose, galactose, ribose, arabinose, xylose, fucose or rhamnose is used as a perbenzylated 1-OH-sugar of formula II.

4. The process according to claim 1, wherein in the alkylating reagent of formula III, the nucleofuge is —Cl, —Br, —I, -OTs, -OMs, —$OSO_2CF_3$, —$OSO_2C_4F_9$ or —$OSO_2C_8F_{17}$.

5. The process according to claim 1, wherein in the alkylating reagent of formula III L means

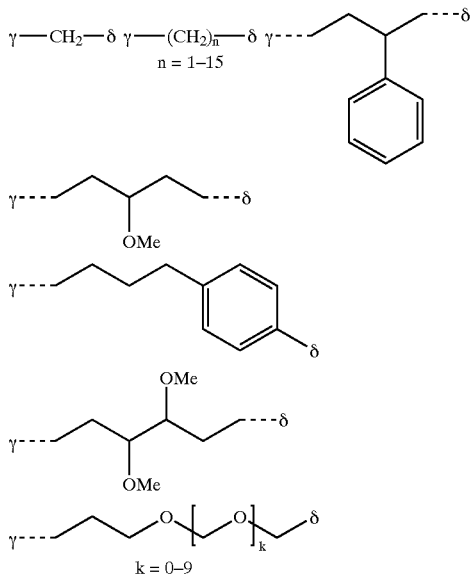

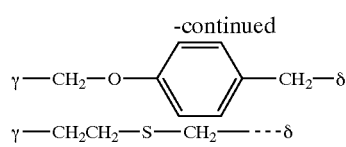
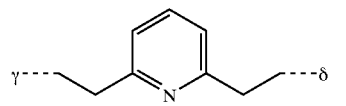
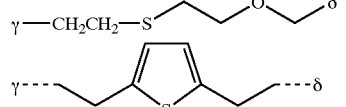
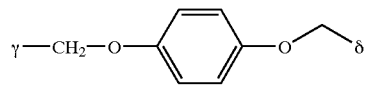
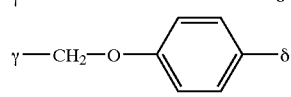
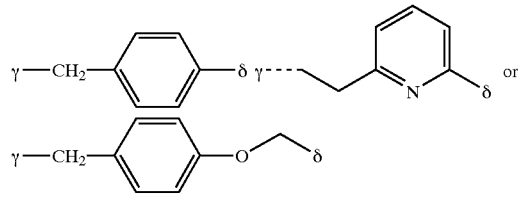
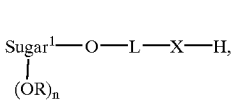

whereby γ is the interface site to sugar, and δ is the interface site to radical X.

6. The process according to claim 1, wherein a water-immiscible solvent is used as an organic solvent.

7. The process according to claim 6, wherein the water-immiscible solvent is toluene, benzene, $CF_3$-benzene, hexane, cyclohexane, diethyl ether, tetrahydrofuran, dichloromethane, MTB or mixture thereof.

8. The process according to claim 1, wherein a quaternary ammonium or phosphonium salt or a crown ether, is used as a phase transfer catalyst.

9. The process according to claim 8, wherein a quaternary ammonium salt is used as a phase transfer catalyst.

10. The process according to claim 1, wherein the base is added in solid form or as a 10–70% aqueous solution.

11. A process for the production of perbenzylated 1-O-glycosides of formula I'

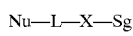

(I')

or a salt thereof,
in which
sugar$^1$ is a monosaccharide that is functionalized in 1-OH- position,
R represents benzyl,
n means 2, 3 or 4,
X means —COO— or —NH—
and
L means a straight-chain, branched, saturated or unsaturated $C_1$–$C_{30}$ carbon chain, which optionally is interrupted by 1–10 oxygen atoms, 1–3 sulfur atoms, 1–2 phenylene groups, 1–2 phenylenoxy groups, 1–2 phenylenedioxy groups, a thiophene radical, pyrimidine radical or pyridine radical, and/or optionally is substituted with 1–3 phenyl groups, 1–3 carboxyl groups, 1–5 hydroxy groups, 1–5 O—$C_1$-$C_7$ alkyl groups, 1–3 amino groups, 1–3 $CF_3$ groups or 1–10 fluorine atoms comprising reacting a perbenzylated 1-OH-sugar of formula II

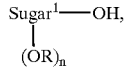
(II)

in which sugar[1], R and n have the indicated meaning, with an alkylating reagent of formula (III)

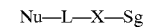
(III), in which Nu means a nucleofuge, L and X have the above-mentioned meaning, and Sg represents a protective group, in an organic solvent in the presence of a base and optionally a phase transfer catalyst at a temperature of 0–50° C., cleaving the protective group, and optionally converting reaction product obtained into a salt.

* * * * *

UNITED STATES PATENT AND TRADEMARK OFFICE
CERTIFICATE OF CORRECTION

PATENT NO. : 6,545,135 B2  
APPLICATION NO. : 09/801050  
DATED : April 8, 2003  
INVENTOR(S) : Johannes Platzek It is certified that error appears in the above-identified patent and that said Letters Patent is hereby corrected as shown below:

Column 18, line 57, reads "of a salt thereof" should read -- or a salt thereof --  
Column 18, line 64, reads "X means —S—,—COO— or —NH—" should read -- X means —S—,—COO— or —NH— --  
Column 19, line 45, reads " 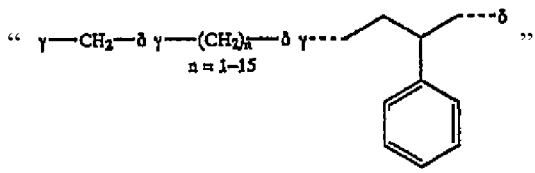 "

should read

-- 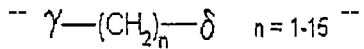

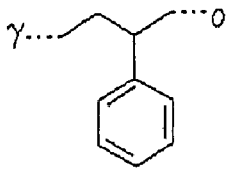 --

Column 20, line 26, reads

" 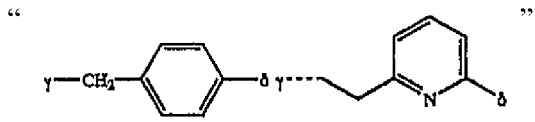 "

should read

-- 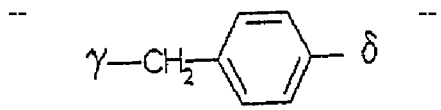

 --

UNITED STATES PATENT AND TRADEMARK OFFICE
CERTIFICATE OF CORRECTION

PATENT NO. : 6,545,135 B2 Page 2 of 2
APPLICATION NO. : 09/801050
DATED : April 8, 2003
INVENTOR(S) : Johannes Platzek It is certified that error appears in the above-identified patent and that said Letters Patent is hereby corrected as shown below:

Column 20, line 43 reads "crown ether, is used as" should read
-- crown ether is used as --

Signed and Sealed this

Thirty-first Day of July, 2007

JON W. DUDAS
*Director of the United States Patent and Trademark Office*